(12) United States Patent
Chinowsky et al.

(10) Patent No.: US 6,480,282 B1
(45) Date of Patent: Nov. 12, 2002

(54) CAPILLARY SURFACE PLASMON RESONANCE SENSORS AND MULTISENSORS

(75) Inventors: Timothy M. Chinowsky; Sinclair S. Yee, both of Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/566,772

(22) Filed: May 8, 2000

Related U.S. Application Data

(60) Provisional application No. 60/132,895, filed on May 6, 1999.

(51) Int. Cl.[7] ................................................ G01N 21/05
(52) U.S. Cl. ........................................ 356/445; 350/246
(58) Field of Search ................................. 356/445, 246

(56) References Cited

U.S. PATENT DOCUMENTS

| | | | |
|---|---|---|---|
| 4,844,613 A | 7/1989 | Batchelder et al. | 356/318 |
| 4,889,427 A | 12/1989 | Van Veen et al. | 356/445 |
| 4,978,503 A | * 12/1990 | Shanks et al. | 356/440 |
| 4,997,278 A | 3/1991 | Finlan | 356/128 |
| 5,023,053 A | 6/1991 | Finlan | 422/82.05 |
| 5,035,863 A | 7/1991 | Finlan et al. | 422/82.05 |
| 5,047,213 A | 9/1991 | Finlan et al. | 422/82.11 |
| 5,047,633 A | 9/1991 | Finlan et al. | 250/306 |
| 5,055,265 A | 10/1991 | Finlan | 422/82.05 |
| 5,064,619 A | 11/1991 | Finlan | 422/82.05 |
| 5,312,535 A | * 5/1994 | Waska et al. | 356/441 |
| 5,313,264 A | * 5/1994 | Ivarsson et al. | 356/445 |
| 5,327,225 A | 7/1994 | Bender et al. | 356/445 |
| 5,359,681 A | 10/1994 | Jorgenson et al. | 385/12 |
| 5,485,277 A | 1/1996 | Foster | 356/445 |
| 5,492,840 A | 2/1996 | Malmqvist et al. | 436/518 |
| 5,647,030 A | 7/1997 | Jorgenson et al. | 385/12 |
| 5,815,278 A | 9/1998 | Johnston et al. | 356/445 |
| 5,822,073 A | 10/1998 | Yee et al. | 356/445 |
| 5,835,645 A | 11/1998 | Jorgenson et al. | 385/12 |
| 5,858,799 A | 1/1999 | Yee et al. | 436/164 |
| 5,991,048 A | 11/1999 | Karlson et al. | 356/445 |
| 6,093,371 A | * 7/2000 | Yasuda et al. | 422/68.1 |

FOREIGN PATENT DOCUMENTS

| | | | | |
|---|---|---|---|---|
| JP | 11-64279 | * | 3/1999 | |
| WO | WO 88/06725 | * | 9/1988 | 351/301 |

OTHER PUBLICATIONS

Boring. C.B. and Dasgupta, P.K. (1997), An affordable high–performance optical absorbance detector for capillary systems, *Analytica Chimica Acta* 342:123–132.

(List continued on next page.)

*Primary Examiner*—Richard A. Rosenberger
(74) *Attorney, Agent, or Firm*—Greenlee, Winner and Sullivan, P.C.

(57) ABSTRACT

SPR sensors and multisensors having capillary geometry. Sensors have a capillary substrate in which at least a portion of the inside surface of the capillary is provided with an SPR-sensing area. Samples for analysis are introduced into the capillary cavity. SPR is measured by radially illuminated the capillary SPR-sensing area with light having a TM-polarized component. Light reflected from the SPR-sensing area exiting radially from the capillary is detected at selected angles to obtain reflectivity as a function of incidence angle to determine RI of the sample in the vicinity of the SPR-sensing area. The capillary geometry is readily adaptable to simultaneous measurement of several optical properties of a given sample in addition to SPR by radial and/or axial illumination of the sample. Multisensors with capillary geometry which simultaneously measure SPR and bulk RI are provided. Multisensors which combine SPR measurements with fluorescence or chemiluminescence, Raman scattering, or absorption measurements are also provided.

25 Claims, 8 Drawing Sheets

OTHER PUBLICATIONS

Brown and Natan (1998), "Hydroxylamine Seeding of Colloidal Au Nanoparticles in Solution and on Surfaces," *Langmuir* 14:726–728.

Chinowsky, T.M. et al. (Jan. 1999), "Optimal linear data analysis for surface plasmon resonance biosensors," *Sensors and Actuators B* 54:89–97.

Chinowsky, T.M. and Yee, S.S. (1998), "Quantifying the information content of surface plasmon resonance reflection spectra," *Sensors and Actuators B* 51:321–330.

Conrad, D.W. et al. (1997), "Photoactivatable silanes for the site–specific immobilization of antibodies," *Proc. SPIE* 2978:12–21.

Evensen, H.T. et al. (Feb. 1998), "Automated fluid mixing in glass capillaries," *Rev. Sci. Instrum.* 69:519–526.

Johnston, K.S. et al. (Jan. 1999), "Performance comparison between high and low resolution spectrophotometers used in a white light surface plasmon resonance sensor," *Sensors and Actuators B* 54:80–88.

Johnston, K.S. et al. (Jan. 1999), "Prototype of a multichannel planar substrate SPR probe," *Sensors and Actuators B* 54:57–65.

Johnston, K.S. and Sinclair, S.Y. (1997), "Calibration of surface plasmon resonance refractometers using locally weighted parametric regression," *Anal. Chem.* 69:1844–1851.

Johnston, K. S. (1995), "New analytical technique for characterization of thin films using surface plasmon resonance," *Mater. Chem. Phys.* 42:242–246.

Jorgenson and Yee, S.S. (1993) "A fiber optic chemical sensor based on surface plasmon resonance," *Sensors and Actuators B* 12:213–220.

Kao, H.P. and Schoeniger, J.S. (Jul. 1998), "Elliptical trough reflector for the collection of light from linear sources," *Appl. Opt.* 37:4194–4199.

Karlsen et al. (1996), "First–order surface plasmon resonance sensor system based on a planar light pipe," *Sensors and Actuators B* 32:137–141.

Kieslinger, D. et al. (1997), Lifetime–based capillary waveguide sensor instrumentation, *Sensors and Actuators B* 38–39:300–304.

Krattiger, B. et al. (Feb. 1993), "Laser–based refractive–index detection for capillary electrophoresis: ray–tracing interference theory," *Appl. Opt.* 32:956–965.

Liedberg, B. et al. (1995), "Biosensing with surface plasmon resonance—how it all started," *Biosensors & Bioelectron.* 10:i–ix;.

Lyon, L.A. et al. (Jan. 1999), "Surface plasmon resonance of colloidal Au–modified gold films," *Sensors and Actuators B* 54:118–124.

Matsuura, Y. and Harrington, J. (Jun. 1997), "Hollow glass waveguides with three–layer dielectric coating fabricated by chemical vapor deposition," *J. Opt. Soc. Am. A* 14:1255–1259.

Melendez, et al. (1996), "A commercial solution for surface plasmon sensing," *Sensors and Actuators B* 35–36:212–216.

Melendez, J. (1997), "Development of a surface plasmon resonance sensor for commercial applications," Sensors and Actuators B 39:375–379.

Misiakos, K. and Kakabakos, S.E., (1998), "A multi–band capillary immunosensor," *Biosensors & Bioelectronics* 13:825–830.

Nenninger et al. (1998), "Reference–compensated biosensing using a dual–channel surface plasmon resonance sensor system based on a planar lightpipe configuration," *Sensors and Actuators B* 51:38–45.

Nikitin, P.I. et al. (Jan. 1999), "Surface plasmon resonance interferometry for biological and chemical sensing," *Sensors and Actuators B* 54:43–50.

Sambles, J.R. et al. (1991), "Optical excitation of surface plasmons: an introduction," *Contemp. Phys.* 32:173–183.

Stellman, C.M. et al. (1998), "A fiber–optic pipette for rapid long–pathlength capillary spectroscopy," *Sensors and Actuators B* 46:56–60.

Tarigan, H.J. et al. (1996), "Capillary–scale refractive index detection by interferometric backscatter," *Anal. Chem.* 68:1762–1770.

Weigl, B.H. and Wolfbeis, O.S. (Oct. 1994), "Capillary optical sensors," *Anal. Chem.* 66:3323–3327.

Wolfbeis, O.S., (1996), "Capillary waveguide sensors," *Trends in Analytical Chemistry* 15:225–232.

* cited by examiner

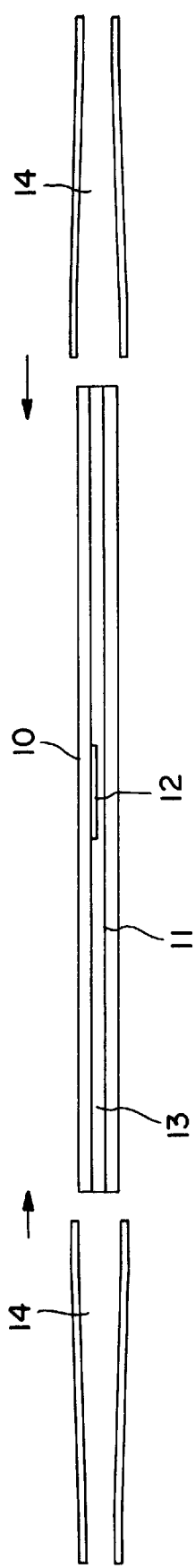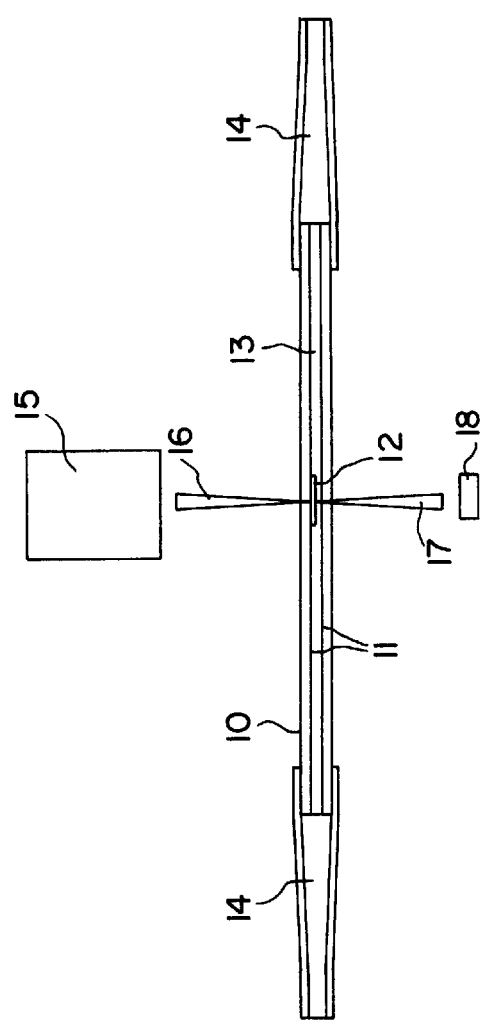

INPUT RAY ELEVATION (y) AS A FRACTION
OF THE OUTER RADIUS

CAPILLARY SURFACE PLASMON RESONANCE SENSORS AND MULTISENSORS

CROSS-REFERENCE TO RELATED APPLICATIONS

This application takes priority from U.S. provisional application Ser. No. 60/132,895, filed May 6, 1999, which is incorporated in its entirety herein to the extent not inconsistent with the disclosure herein.

BACKGROUND OF THE INVENTION

This invention relates generally to Surface Plasmon Resonance (SPR) sensor devices, their use in biological and chemical sensing, and their use in multisensor devices and applications.

Field-based biological and chemical sensors are of increasing importance due to their ability to detect natural and man-made hazards such as environmental contamination, biowarfare agents, explosives, and food-borne pathogens. Optical sensors based on surface plasmon resonance (SPR) are attractive for these applications.

Surface plasmon resonance (SPR) is an optoelectronic phenomenon used to construct sensitive thin-film refractometers which may be readily applied to chemical and biological sensing (Liedberg, B. et al. (1995), "Biosensing with surface plasmon resonance—how it all started," Biosensors & Bioelectron. 10:i–ix; Sambles, J. R. et al. (1991), "Optical excitation of surface plasmons: an introduction," Contemp. Phys. 32:173–183). One common design of an SPR sensor is shown in FIG. 1a. A prism (1) is coated on one side (2) with a 50 nm gold (or silver) film (3). Monochromatic light (4, TM polarized) enters an opposing prism face and strikes the metal-coated face (2) at a range of angles above the critical angle. The reflected light (5) is measured, and reflectivity (intensity of reflected light) as a function of angle is determined. When plotted, this reflectivity spectrum exhibits an attenuation feature centered at a particular angle (FIG. 1b). This angle is sensitive to the refractive index (RI) within approximately one wavelength of the metal-coated surface: If the RI increases, e.g., due to the presence of an analyte, the angle will increase, as illustrated in FIG. 1b for RI=$n_a$=1.33–1.38. Measurement of this angle can be used to measure the effective RI of a thin layer adjacent to the metal surface and to detect changes in RI due to changes in type and concentration of analytes present in that layer.

The planar SPR configuration has practical constraints, including awkward sample handling, requirements for index matching and optical inflexibility, that limit its application. For most SPR sensing experiments, the analyte must smoothly and continuously flow over the planar sensing surface. As illustrated in FIG. 1a, a flat flow cell sealed to the metal surface using gaskets and incorporating input and output fittings for tubing connections is typically employed. Because of the complexity of construction of the cell, sample handling can be awkward and leaks and bubble accumulation, which disrupt sensing, are common problems. Because the prism used in the planar configuration can be an expensive glass component, the SPR metal layer is often deposited on a thin disposable glass slide which is index-matched to the prism. The inexpensive slide may then be changed without disturbing the prism. The use of an index-matching fluid introduces additional complexity in the device, difficulty of use, and other problems including potential sensor drift and analyte contamination. The planar SPR configuration is not readily adaptable to multisensing applications (e.g., simultaneous measurement of several sample properties, particularly optical properties). The planar configuration is designed to measure reflectivity only and only one side of the planar sensing surface is optically accessible. This configuration does not allow other types of optical measurements (e.g., transmissivity or fluorescence) which are of interest in multisensing applications.

SPR sensing technology can be adapted for field sensing applications by improving sensor compactness, ruggedness, and ease of use and by improving the optical flexibility of the SPR sensor by facilitating its use for multiple independent optical measurements.

Several improved sensing SPR configurations, including the ultraminiature fiber-optic SPR probe developed by Jorgenson and Yee, S. S. (1993) "A fiber optic chemical sensor based on surface plasmon resonance," Sensors and Actuators B 12:213–220, the SPR lightpipe developed by Karlson et al. (1996), "First-order surface plasmon resonance sensor system based on a planar light pipe," Sensors and Actuators B 32:137–141, in which the optical substrate may be replaced without the use of index matching fluid, and a miniature planar probe sensor combining the advantages of these devices (Johnston, K. S. et al. (1999), "Prototype of a multi-channel planar substrate SPR probe," Sensors and Actuators B 54:57–65). Another recent development is a compact, rugged integrated SPR sensor in which all sensor components are contained in one small molded package (Melendez, J. (1997), "Development of a surface plasmon resonance sensor for commercial applications," Sensors and Actuators B 39:375–379).

Several multisensor configurations of SPR devices have been reported. Johnston et al. described how simultaneous measurement of multiple lightpipe sensor "bands" improves the ability of SPR measurements to characterize thin films (Johnston, K. S. (1995), "New analytical technique for characterization of thin films using surface plasmon resonance," Mater. Chem. Phys. 42:242–246.). Nenninger et al. (1998), "Reference-compensated biosensing using a dual-channel surface plasmon resonance sensor system based on a planar lightpipe configuration," Sensors and Actuators B 51:38–45 demonstrated the use of multichannel sensing in the lightpipe geometry to compensate for non-specific binding in SPR biosensing. Chinowsky et al. described the combination of bulk refractive index (RI) measurements with SPR measurements to compensate for interference from temperature or buffer concentration changes (Chinowsky, T. M. and Yee, S. S., U.S. Provisional Application No. 60/132,894, filed May 6, 1999, incorporated by reference herein in its entirety). Chinowsky et al. also demonstrated the use of estimation theory to design optimal linear data analysis techniques for SPR (Chinowsky, T. M. et al. (1999), "Optimal linear data analysis for surface plasmon resonance biosensors," Sensors and Actuators B 54:89–97) and to quantify the ultimate capabilities of such combination measurements (Chinowsky, T. M. and Yee, S. S. (1998), "Quantifying the information content of surface plasmon resonance reflection spectra," Sensors and Actuators B 51:321–330). In related research, Johnston et al. demonstrated a chemometric approach to SPR data analysis and calibration (Johnston, K. S. et al. (1997), "Calibration of surface plasmon resonance refractometers using locally weighted parametric regression," Anal. Chem. 69:1844–1851), and showed that such an approach can enable simplifications in sensor instrumentation (Johnston, K. S. et al. (1999), "Performance comparison between high and low resolution spectrophotometers used in a white light surface plasmon resonance sensor," Sensors and Actuators B 54:80–88).

The present invention overcomes limitations of currently available SPR configurations by providing a novel device configuration that is less complex, simpler to use and adaptable to multisensor applications.

SUMMARY OF THE INVENTION

The present invention provides a capillary SPR sensor. This sensor comprises a capillary substrate, i.e., a tube with an axial cavity, in which at least a portion of the inside surface of the capillary is provided with an SPR-sensing area. The SPR-sensing area comprises an SPR-active conductive layer, which can be a among others, a metal layer (particularly gold or silver), a semiconductor layer or an organic conductor layer. In this SPR sensor configuration, a sample to be analyzed is introduced into the capillary cavity and the capillary substrate is then radially illuminated with light having a TM-polarized component. Light exiting radially from the capillary substrate is detected at selected angles. Radially exiting light that interacts with the SPR-sensing area at angles greater than the critical angle carries SPR features. This light can be detected as a function of incident angle to detect SPR, measure the refractive index of an analyte in the sample, and detect the presence of an analyte in the sample.

In a specific device configuration, an SPR sensor of this invention comprises a substantially transparent capillary substrate having one or more SPR-sensing areas on the inside surface of the capillary, a light source for radially illuminating the SPR-sensing areas at incident angles above the critical angle and a detector for detecting light reflected from one or more SPR-sensing areas of the capillary substrate as a function of incident angle. The light source can be collimated and optionally focused with a lens that is optically coupled to the light source at or near the SPR-sensing area (e.g., the inside surface of the capillary). In operation, the SPR-sensor is provided with means for introducing and removing samples from the capillary substrate. The sensor can be configured for measurement of static samples or for flowing samples.

An SPR-sensing area can comprise a dynamic range-controlling layer adhered to the SPR-active conductive layer to alter the dynamic range of the SPR sensor.

An SPR-sensing area can comprise one or more reactive layers in contact with the SPR-conductive layer which interact with one or more selected analyte species, which may be present in a sample, to change the effective RI detectable by the sensor. A reactive layer can be a biologically reactive layer exhibiting a selective interaction with a biological molecule, e.g., with a selected antigen, protein, peptide, nucleic acid, or related species. A given capillary substrate can be provided with one or more SPR-sensing areas each of which have the same or different reactive layers which are selective for detection of the same or different analytes.

The invention further provides a multisensor comprising a capillary tube substrate having one or more SPR-sensing areas on its inside surface. A multisensor is configured for measurement of at least one optical property of a sample in addition; to SPR. A multisensor of this invention can, for example, be configured to measure bulk RI by critical angle refraction or interferometric methods, fluorescence, chemiluminescence, absorption or Raman scattering of a sample at one or more wavelengths of light. Dependent upon the optical measurements to be performed, the multisensor is provided with one or more light sources to provide for radial or radial and axial illumination of the capillary substrate containing the sample. Also dependent upon the optical measurements to be performed, the multisensor is provided with one or more detectors of radially or axially reflected, refracted, emitted or transmitted light. Dependent again upon the types of optical measurements to be made, the inside surface of the capillary tube substrate is selectively patterned with one or more SPR-sensing areas to provide transparent regions on the inside surface for illumination of the sample in the capillary tube. SPR-sensing areas can be provided at various locations along the inside surface of the capillary and are positioned to allow simultaneous SPR measurement as well as measurement of other optical properties. For simultaneous measurement of SPR and bulk RI only a small region of the capillary need be left uncoated. In specific embodiments, a capillary substrate useful in multisensors of this invention can be provided with an SPR-sensing area on one lengthwise end of the inside surface of the capillary while the other end is uncoated. In an alternate embodiment, a radial section of the inside capillary surface is provided with the SPR-sensing area while the remaining radial section remains uncoated. Similarly, reactive layers can be selectively patterned on the SPR-sensing areas. For example, one or more SPR-sensing areas can be provided with one or more separate reactive layers that are selective for different chemical or biological species.

In specific embodiments, the invention provides multisensor devices which (1) allow measurement of both SPR and bulk refractive index of a given sample; (2) allow measurement of SPR and fluorescence or chemiluminescence of a given sample; or (3) allow measurement of SPR and an absorption or Raman scattering spectrum of a given sample. The invention provides for multisensors in which any one or more emission, refraction, reflection or absorption optical measurements are combined with SPR. Fluorescence or chemiluminescence measurements may require selective labeling of an analyte of interest.

The invention also provides a method for detecting the presence of one or more selected analytes (including biological molecules) in a sample employing an SPR sensor or multisensor device of this invention.

The capillary substrates of this invention can be provided in kits for analysis of selected analytes. A kit contains one or more optionally disposable capillary substrates each provided with one or more SPR-sensing areas which may be patterned on the inside surface of the capillary optionally combined in a kit with analyte control sample(s) for control measurements or device calibration. In specific embodiments, an analysis kit contains one or more capillary substrates provided with one or more SPR-sensing areas each of which sensing areas has a reactive layer selective for a given analyte. A kit can contain one or more capillary substrates having the same or different reactive layers which can be selectively for the same or different analytes. Kits include those that contain capillary substrates having biologically reactive layers that are selective for the same or different biological analytes, e.g., one or more proteins, peptides, nucleic acids or antigens. Kits can also be provided containing one or more capillaries provided with one or more SPR-active conductive layers and reagents for selective introduction of one or more reactive layers on the conductive layers.

The capillary SPR sensor geometry of this invention provides significant improvements in sample handling by providing a capillary sample cell for smooth flow and easy fluid connections; significant improvements in device simplicity and cost by providing one-piece inexpensive optics requiring no index matching and that can employ inexpensive, mass-produced glass tubes as disposable optical sensing elements; and significant improvements in optical flexibility by providing for the use of optical techniques in addition to SPR, such as transmission measurements, bulk refractometry, and fluorescence for analyte analysis.

Multisensor configuration of this invention combine multiple optical measurement technologies in a compact, field-applicable device. These sensors exploit the previously demonstrated benefits of multichannel SPR sensing and bulk RI compensation, while extending the sensor capabilities to include other optical measurement techniques, including bulk and evanescent fluorescence, interferometric RI measurement techniques, absorption, and Raman scattering.

In addition, the use of the capillary substrate protects the SPR-sensing surface from contamination, and (with the addition of end caps) forms a convenient optionally disposable container allowing the environment surrounding the sensing surface to be controlled during storage.

Other advantages and benefits of this invention will be readily apparent on consideration of the following detailed description.

BRIEF DESCRIPTION OF THE FIGURES

FIG. 2a is a side view illustration of the capillary SPR sensing geometry.

FIG. 2b is a side view of a capillary SPR sensor of this invention containing the SPR capillary of FIG. 2a.

FIG. 2c is a cross-sectional view illustration of radial illumination of a capillary of FIG. 2a.

DETAILED DESCRIPTION OF THE INVENTION

The invention is further illustrated by reference to the drawings where the same numbers are used to indicate like features.

Figure 1A:
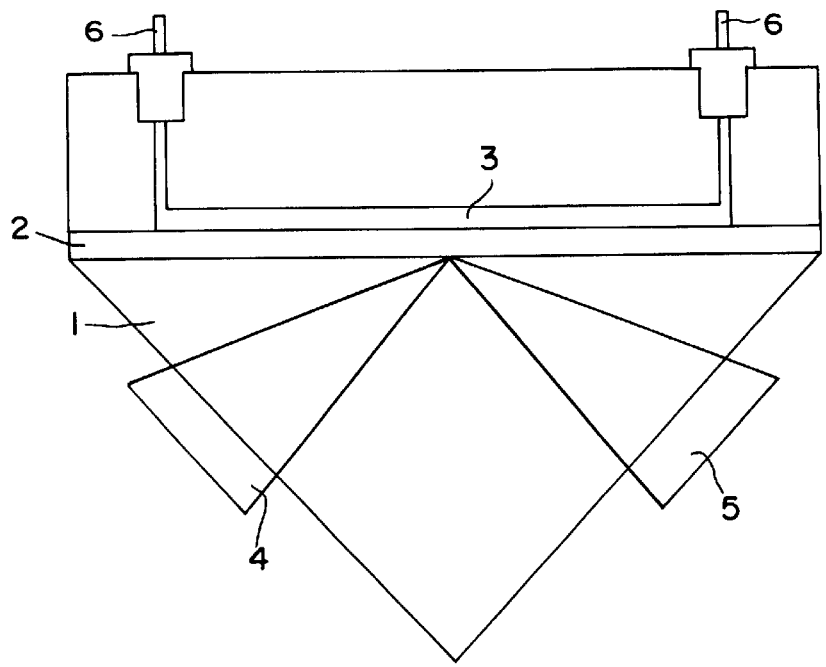
FIG. 1a is an illustration of the planar SPR configuration.
Figure 1B:
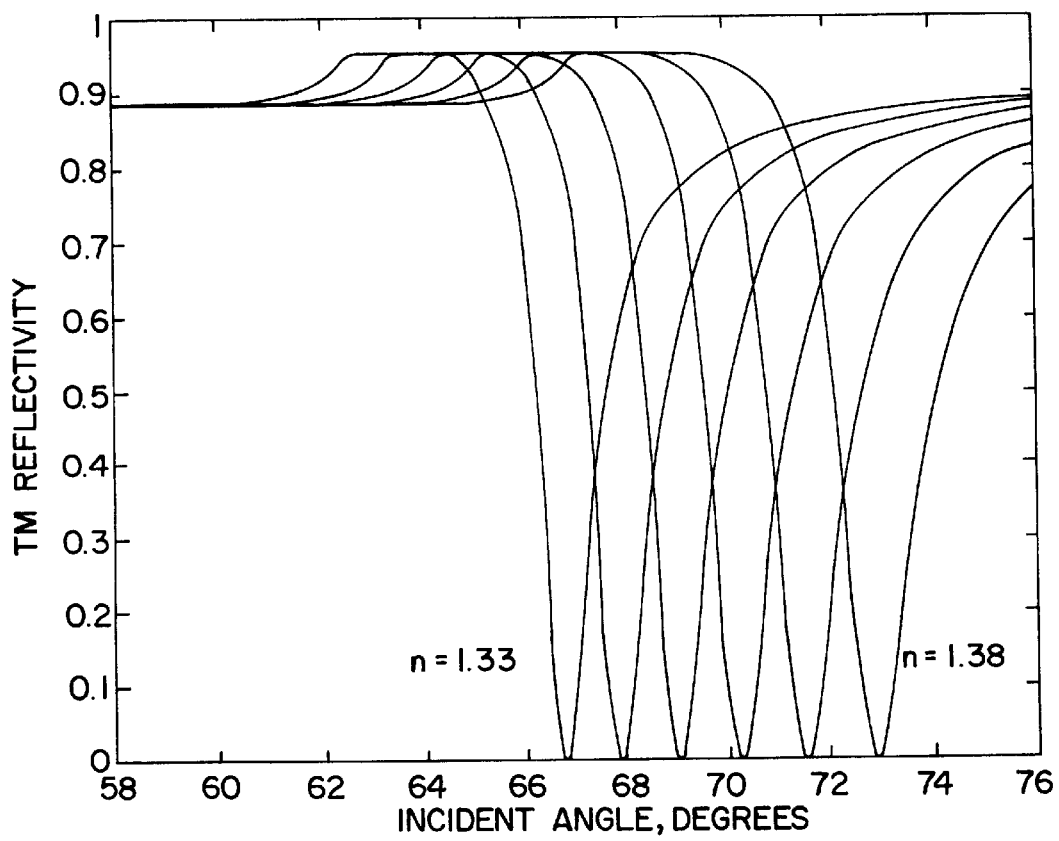
FIG. 1b is a graph of simulated SPR reflection spectra of TM reflectivity as a function of incident angle for samples varying in n (RI) from 1.33 to 1.38.

In the planar SPR configuration as illustrated in FIG. 1a, a prism (1) is coated on one side with an SPR-conductive layer (2). Typically, the coating is provided on a glass slide that is then index matched to the prism surface. Monochromatic light (4) enters an opposing face of the prism and strikes the SPR-conductive layer at a range of angles above the critical angle. Light reflected from the SPR-conductive layer (5) is detected and reflectivity is graphed as a function of incidence angle. The planar SPR sensor is provided with a flow cell (3) with fluid connections (6). The reflectivity spectrum exhibits an attenuation feature centered at a particular angle, as illustrated in FIG. 1b. This angle is sensitive to the refractive index (RI) of the analyte within approximately one wavelength of the SPR-active conductive layer. The angle at which the attenuation feature is observed increases if the RI in this region increases. Determination of the angle at which the SPR feature is observed measures the effective RI in the thin film adjacent to the SPR-conductive layer. As indicated in FIG. 1b, the SPR feature when the analyte has RI (n)=1.33 will be at a lower angle the SPR feature when the analyte has RI(n)=1.38.

Figure 2C:
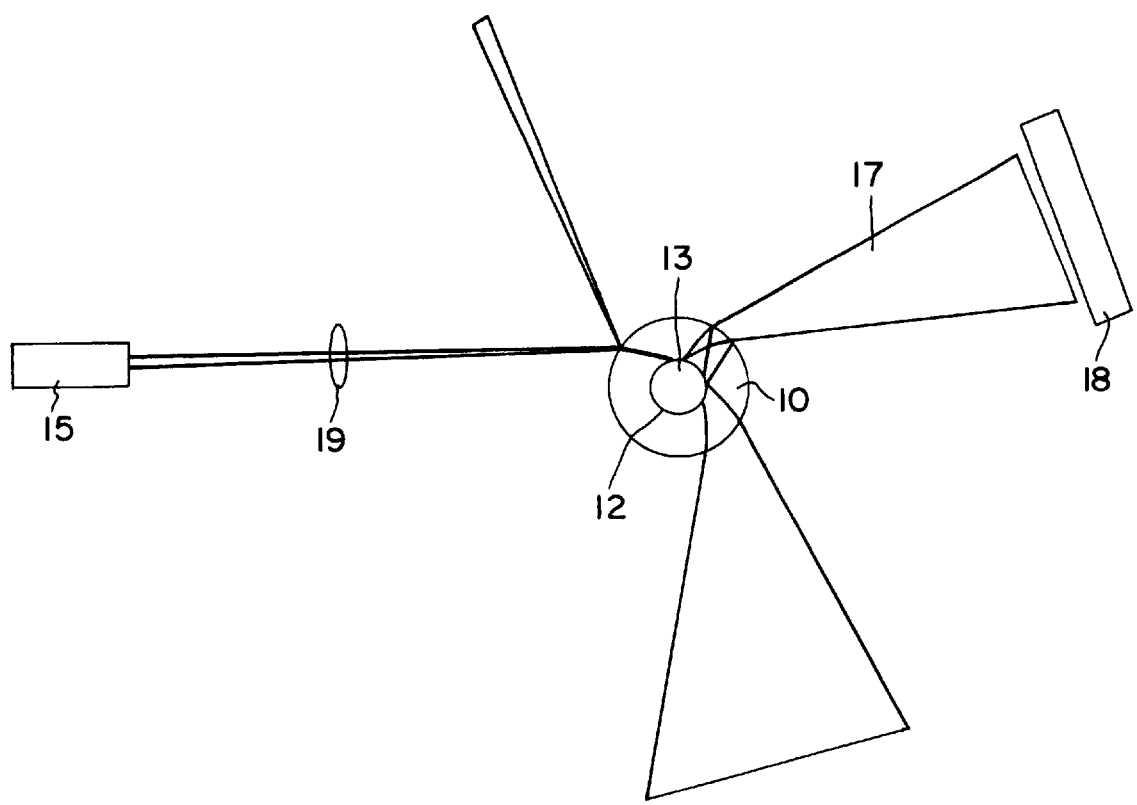

FIG. 2a illustrates a side view of a capillary SPR configuration of this invention. A capillary substrate (10) is provided with at least one SPR-sensing area (12) on the inside surface (11) of the capillary tube. The capillary substrate is connected at both ends, e.g. via tubing (14), to a sample handling system (not shown), to introduce samples into the capillary cavity (13). FIG. 2b illustrates a capillary SPR sensor of this invention in which the capillary substrate (10) is positioned to be radially illuminated by light from light source (15). Incident light (16) interacts with an SPR-sensing area (12) having at least one SPR-sensing area and is reflected radially (17) to be detected by detector (18). Incident light (16) is illustrated in FIG. 2b as being focused at (or near) the SPR-conductive layer, however focusing is not required. Incident light contains a TM-polarized component and may be composed substantially of TM polarized light. FIG. 2c illustrates a cross-section of a radially illuminated capillary of FIG. 2b. Collimated light from the light source (15), e.g., a laser diode, focused with a converging lens (19) at or near the surface of the capillary hits the SPR-conducting layer and is reflected at the diverging mirror surface. Reflected light exits the capillary radially at a range of angles as illustrated. The detector (18), which is illustrated as a diode array, is positioned to detect light that carries SPR, e.g., light that hits the SPR-sensing area at angles greater than the critical angle. The angle at which the light exits the capillary after interacting with the SPR-sensing area corresponds to the incidence angle so that detection of exiting light as a function of angle results in a reflectivity vs. angle measurement and allows measurement of RI of the sample in the capillary cavity. SPR sensors may also be used to detect changes in RI in a flow system to detect changes in flow or to specifically detect the presence of an analyte in a flowing sample.

Capillary Optics

When a radial incident ray strikes the exterior surface of a capillary with incident angle $\theta_o$, the refracted ray strikes the interior surface at an angle $\theta_i$ given by:

$$\sin\theta_i = \frac{r_o}{r_i}\frac{n_o}{n_i}\sin\theta_o$$

where $r_o$ and $r_i$ are the outer and inner radii of the capillary, respectively, $n_i$ is the RI of the capillary itself and $n_o$ is the RI of the medium surrounding the capillary (typically air, $n_o$=1). For a thick wall capillary, defined as one for which:

$$\frac{r_o}{r_i}\frac{n_o}{n_i} \geq 1.$$

Figure 3A:
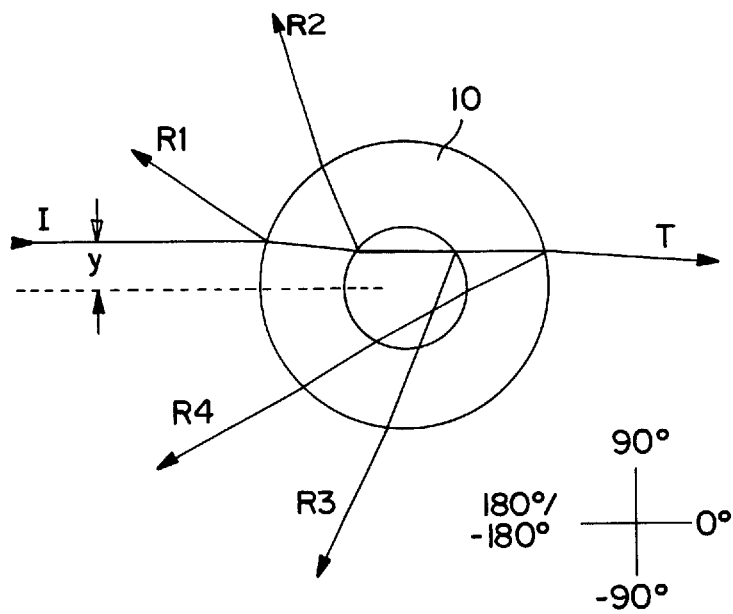
FIG. 3a illustrates the radial geometry of a water-filled glass capillary under TM-polarized radial illumination.
Figure 3B:
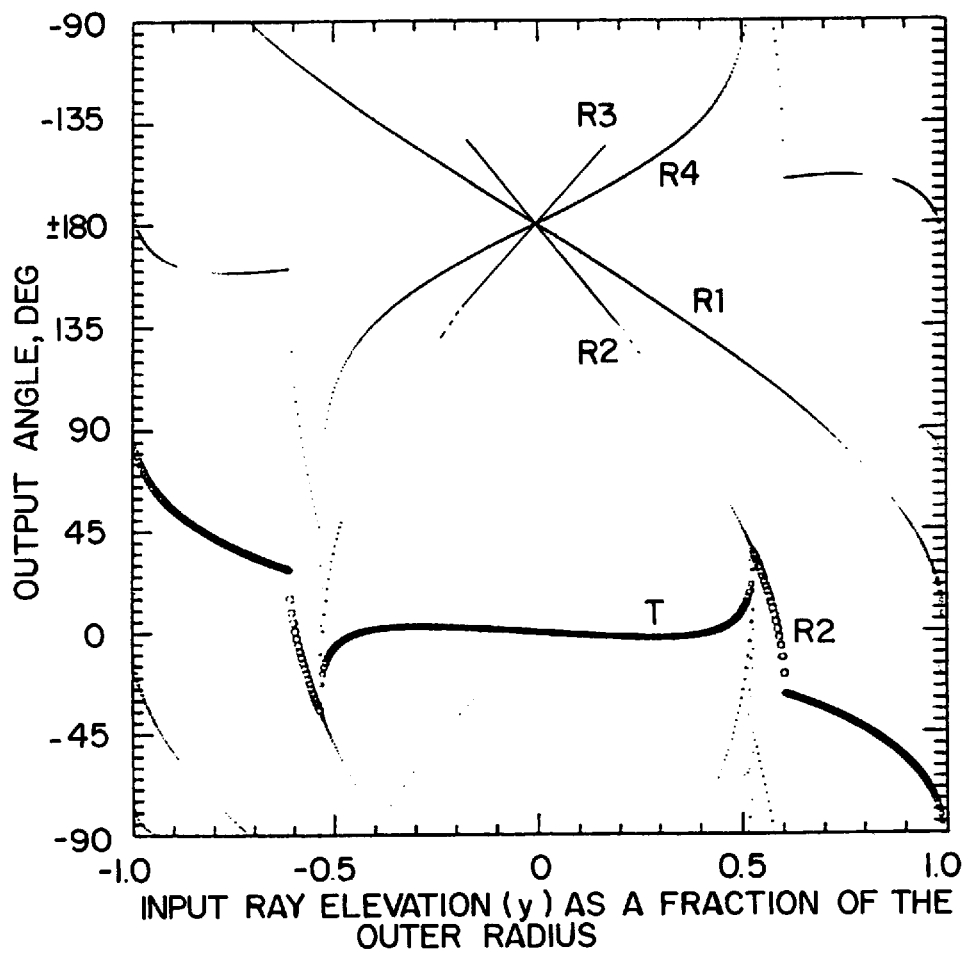
FIG. 3b is a graph of a simulation of the optical response of an uncoated capillary (1 mm OD, 0.4 mm ID, incident light 670 nm TM polarized, water-filed capillary) plotting ray Lo intensity as function of exit angle θ and input ray elevation y. For simplicity, only rays with intensity greater than or equal to 1% of the incident intensity are shown.

$\theta_o$ may be chosen such that the refracted ray strikes the internal wall of the capillary at any angle ranging from 0° to 90°. FIGS. 3b and c show geometrical optics simulations of the reflections and refractions that result when an optical "ray" strikes a water-filled glass capillary, assuming that the incoming rays are horizontal and with elevation y relative to the center of the capillary. FIGS. 3b and c graph the intensity and exit angle θ of each ray leaving the capillary and correspond to an uncoated capillary and a capillary coated with a thin conducting layer (e.g., metal), respectively. FIG. 3a shows, for a sample ray, the most significant reflections that occur. In both FIGS. 3b and c, the intensity of each exit ray is indicated by the diameter of the plot point.

Figure 3C:
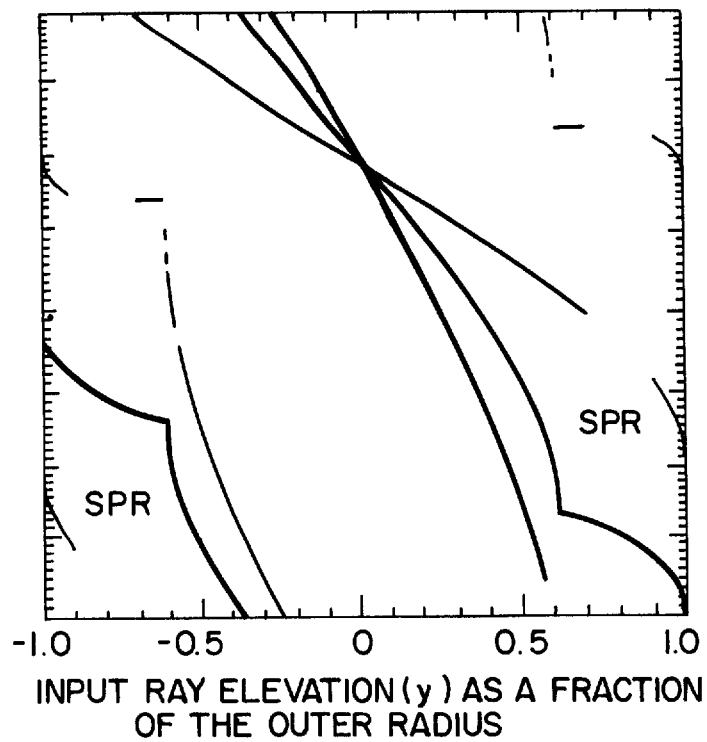
FIG. 3c is a graph of a simulation of the optical response of a capillary like that of FIG. 3b, but having an approximately 50 nm gold layer applied at the inside surface of the capillary. For simplicity, only rays with intensity greater than or equal to 1% of the incident intensity are shown.

The optical response of FIG. 3b exhibits three distinct regions. In the internal transmission region (|y|<0.55 in FIG. 3b), the ray strikes the interior surface of the capillary below the critical angle; in the total internal reflection region (0.55<|y|<0.6), the ray strikes above the critical angle; and in the external transmission region (|y|>0.6), the ray does not strike the interior surface at all, but passes directly through the wall of the capillary. FIG. 3c exhibits similar regions.

The optical response of a glass capillary internally coated with thin metal or dielectric films can be simulated by calculating the reflection at each interface using a multilayer Fresnel model. With this modification to the simulation, the SPR phenomenon appears as an intensity modulation of the most prominent ray in the TIR region, as illustrated in FIG. 3c. Conceptually, the optical response of the capillary may be probed using a collimated bundle of rays adjusted to strike the capillary at particular elevations. For the capillary illustrated in FIG. 3a, a bundle of rays extending from y=0.55 to y=0.6 would strike the internal surface at angles ranging from the critical angle to 90° and exit the capillary at angles ranging from 30° down to −25°. Since each exit angle corresponds to a different internal angle of incidence, a detector intercepting some range of output angles will yield a measurement of reflectivity vs. angle.

If a range of y values is illuminated, rays will exit the capillary at a range of angles. This "fan" of rays can be projected onto a linear array detector or other detector. To increase illumination in the region of interest for SPR, a focused light beam can be used. A focused beam is Gaussian in nature; it has nonzero divergence and has a beam waist (i.e., minimum focus spot) inversely proportional to the divergence. Because the divergence is still small (a few degrees) the beam can be roughly modeled as a collimated beam with a width that varies with distance from the focus. The beam is moved back and forth (moving the capillary toward (closer to) or away from (farther from) the focus) to increase or decrease, respectively, the range of y that is illuminated. The beam is moved from side to side (with respect to alignment with the capillary) to change the value of y at which the illumination is centered.

Focus of the light source can be positioned by reference to FIG. 3a. This illustration shows the relationship between input ray elevation and output ray angles. For example, the rays labeled "R2" are the rays which reflect from the internal surface of the capillary; these are the important rays for looking at SPR and the critical angle. At y=0, the ray is incident on the internal surface at 0°; at the end of the trace of R2 (at y~=0.6) the ray is incident at 90°. The critical angle is located on this trace at the cusp between ray "T" and ray "R2" (at y~=0.55). To monitor the critical angle, rays with lower values of y (i.e., with incident angles lower than the critical angle) are detected; to look at SPR, rays with higher values (i.e., with incident angles higher than the critical angle) are detected.

In practice, the beam is aligned by looking at the output rays while adjusting the focus position. The projection of the output rays indicates what range of y is illuminated. The beam is then moved from side to side to select a different region of the response, and back and forth to change the size of the region. For example: if at the start, the brightest exit spot is centered around −80°, the beam is illuminating y values around 0.9. Moving the beam sideways, closer to the center of the capillary (and to y=0) the exit spot will move to lower angles, say to cover a range of −45.° to 45°. Then, moving the focus closer to the capillary, this range may be decreased to −25°—35°. When this is achieved, according to FIGS. 3a–c, we know that the internal surface of the capillary is illuminated only above the critical angle.

FIGS. 4a–e depicts the capillary optical response under several different conditions. To measure the optical response, a 632.8 nm He—Ne laser was used for radial illumination, and the detector used was a hemicylindrical screen of photosensitive paper. Radial emission from the capillary could thus be recorded over a full 180 degrees. The laser beam was focused using a 10×microscope objective. A capillary holding fixture was mounted on an X-Y translation table near the focus of the laser beam. Capillaries were mounted in the positioning fixture and tubing attached to the capillary to enable fluid flow through the capillary cavity. The position of the capillary with respect to the beam of light was then adjusted to illuminate the desired range of angles. Although the focused Gaussian beam used to obtain the data in FIGS. 4a–e is different from a bundle of geometrical optical rays, the capillary optical response observed was found to qualitatively agree with that predicted by the simulations performed. As the capillary was moved across the beam, the distribution of exit angles was found to vary in a manner consistent with FIGS. 3b and c. As the capillary was moved nearer or farther from the focus of the light beam, the range of output angles varied in a manner predicted by FIGS. 3b and c for a narrower or wider bundle of rays.

Figure 4A:
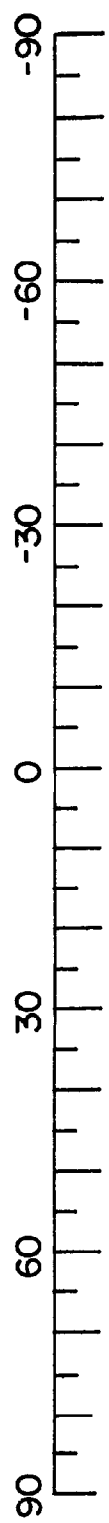
FIGS. 4a–e illustrate the photographically recorded optical responses of a radially illuminated SPR capillary. The capillary (1 mm OD; 0.4 mm ID) was uncoated (a and b) or provided with a Au surface (c–e). The capillary in a–d was filled with water. The capillary in e was filled with ethanol. The capillary was illuminated using a 632.8 nm He—Ne laser beam focused using a 10×microscope objective.
Figure 4B:

FIGS. 4a and 4b show the response of an uncoated glass capillary (1 mm, OD; 0.4 mm ID) under TE and TM illumination, respectively, adjusted to strike a broad range of angles and to highlight the region of the capillary response corresponding to reflections from the internal surface below the critical angle (30° to 90° in FIG. 4a–e). Note that, as expected, TE reflectivity is greater in this region. Also note the fringes (−30° to 30° in FIG. 4a–e) resulting from the interference of rays which travel different optical paths through the capillary, but emerge at the same angle. Such fringes may be exploited for interferometric RI sensing, as will be discussed below.

Figure 4C:
Figure 4D:
Figure 4E:
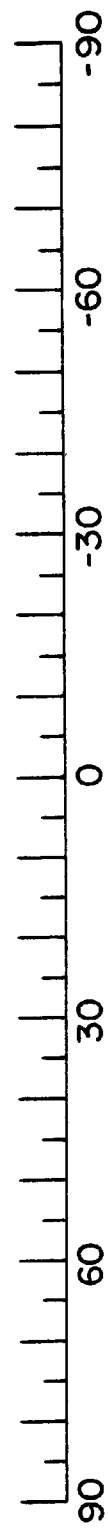

FIGS. 4c and 4d show the response of a water-filled capillary of the same dimensions which has been internally coated with approximately 50 nm of gold using the wire method described below. Illumination was adjusted to strike only the region above the critical angle, and so no fringes are seen. The TE response (FIG. 4c) is uniform, while the TM response (FIG. 4d) shows the localized attenuation characteristic of SPR. FIG. 4e shows the TM response when the capillary is filled with ethanol (n=1.36) compared to water (n=1.33); as expected, the attenuation moves to a lower angle on the screen (corresponding to a higher angle on the capillary's internal surface).

These results demonstrate that critical angle sensing (to determine bulk RI) and SPR sensing are both possible in the capillary geometry, and that geometrical optics discussed above and illustrated in FIG. 3a–c qualitatively describe the capillary response.

The capillary SPR configuration requires the deposition of an SPR-active conducting layer (12) on the inside surface of the capillary. A thin metal layer, preferably a gold or silver layer, of about 40–100 nm (typically 50 nm) in thickness is a useful SPR-conducting layer. Several methods have been found to provide SPR-active conductive metal layers inside of capillary tubes.

High-angle bulk evaporation can be employed for capillary tubes with relatively large inner diameter (preferably for tubes with ID in the range of about 1 mm or more). The capillary tubes may simply be placed in a conventional thermal or electron-beam evaporator with their axis at an angle with respect to the normal to the evaporation source. This allows evaporated metal to reach the inner surface of the capillary. Angles from about 1° to about 10° degrees have been used to successfully deposit layers. If the capillary is stationary during the evaporation, the coverage inside the capillary (as measured by the fraction relative to the coverage of a normal surface) will vary with the angular position and distance inside the capillary. The nonuniformity of the layers deposited by this method does not present a significant problem, because only a small spot of metal is needed for sensing, and a sufficiently uniform spot may be found. Alternatively, the capillary can be rotated during deposition, the metal coverage will then have angular uniformity, and vary only with distance inside the capillary. This method is exemplified in Example 1A.

Figure 5:
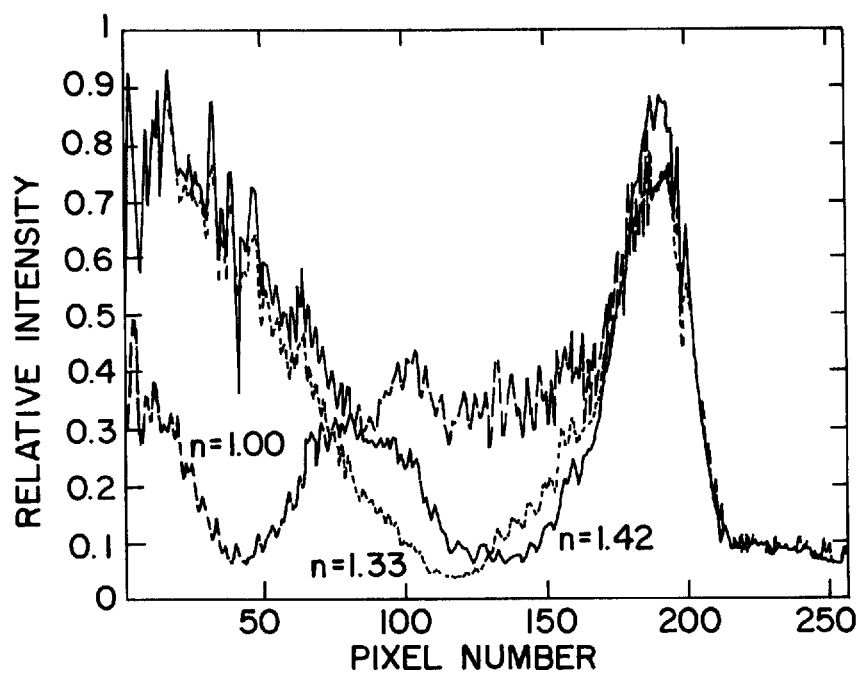
FIG. 5 is a graph of relative intensity of reflected light as a function of pixel number (corresponding to exit (and incidence) angle) from a capillary SPR sensor as described in Example 1A for air (n=1.0), water (n=1.33) and ethylene glycol (n=1.42) samples in the capillary.

SPR measurement made with a capillary sensor prepared as described in Example 1A are shown in FIG. 5. As seen in the three representative graphs shown in FIG. 5, the reflection spectra exhibit an attenuation feature which moves to higher pixel numbers (higher angles) as the analyte RI increases.

Wire evaporation can also be employed for depositing a metal layer inside capillaries, as exemplified in Example 1B. This method makes use of thin metal-coated tungsten wire (preferably gold-coated). While the wire is held in the center of the capillary under low vacuum, a current pulse is sent through the wire, heating it and evaporating the coated metal onto the capillary interior. The amount of metal deposited can be controlled by selecting the wire diameter, thickness of metal coated on the wire, for a given capillary ID. An adhesion layer can be provided prior to evaporation to enhance adhesion of the metal layer to the capillary surface.

A wet chemical process for depositing SPR-quality gold layers on glass has been demonstrated by Brown and Natan (1998), "Hydroxylamine seeding of colloidal Au nanoparticles in solution and on surfaces," Langmuir 14:726–728. In this two-step process, gold colloid particles are fastened to the glass surface using mercaptopropylsilanes, and then additional gold is reduced from a gold chloride solution onto the surface using hydroxylamine. The colloid particles act as seeds, and grow into a uniform layer as the reduction proceeds. This method can be readily adapted for the deposition of metal SPR-conducting layers on the inside surface of a capillary.

Capillaries useful in the SPR devices of this invention can range widely in size and length. Preferred capillary IDs range upward from about 10 $\mu$m. It is desired that light strike the capillary interior surface at a full range of angles (0 to 90°). To achieve illumination at this full range of angles, the ratio between the capillary OD and ID are preferably equal or greater than the ratio between the RI (refractive index) of the capillary material and the external RI (typically air). So, for a glass capillary with RI 1.5, the OD/ID ratio of the capillary should preferably be at least about 1.5. The capillary is made of material that is transparent or substantially transparent at the wavelengths of light that are to be used for sensing applications. Soft glass, fused silica or other materials can be employed for capillaries.

Details of certain SPR configurations are provided in U.S. Pat. Nos. 5,815,278; 5,822,073; 5,064,619; 5,055,265; 5,047,633; 5,047,213; 5,035,863; 5,023,053; 4,997,278; 4,889,427; and 5,485,277, which are incorporated in their entirety by reference herein to the extent not inconsistent herewith for descriptions of SPR configurations and general principles of SPR. A variety of methods for providing reactive layers are known in the art and can be readily adapted for use in the capillary configurations herein.

An SPR sensing area comprises one or more layers which together support SPR. The sensing area comprises an SPR-active conductive layer, i.e. a layer that supports SPR This layer may be a conductor, e.g., a metal layer that supports SPR or a semiconductor layer that supports SPR. Semiconductors useful in the conductive layer include silicon and germanium. Alternatively, conductive polymers can be used in the conductive layer. The conductive layer can be a "SPR-supporting metal layer" which herein means a highly-reflective metal that supports SPR at the metal-sample interface and has a permittivity constant wherein the real part of the permittivity is negative and its magnitude is greater than the magnitude of the imaginary part. For wavelengths in the visible and near-infrared (i.e., 400 nm–1, 000 nm), both silver and gold satisfy this criterion. The SPR supporting metal can also be a mixture of one or more metals or be composed of sequential layers of different metals. If the wavelength range utilized extends into the infrared, other metals, such as aluminum, copper, and tantalum, may also be used.

Preferably the SPR-active conductive layer, e.g., the metal layer, is adhered to the sensor surface (i.e., the surface that will contact samples containing analyte) to a thickness which will optimize the measured resonance curve, i.e., to a thickness which makes the SPR resonance spectrum both deep and sharp, between about 40 nm to 70 nm thick. When the SPR-supporting metal layer is made of silver, the layer thickness preferably is between about 50 nm to 55 nm thick. Layers of silver thinner than about 40 nm result in substantially shallow and broadened resonances, and layers thicker than about 60 nm will result in significant diminishment or disappearance of the resonance feature. The range of thicknesses for gold SPR-supporting layers are also 40–70 nm, preferably 50–60 nm. Gold is preferred because of its inertness and resistance to oxidation. SPR-supporting metal layers can be prepared with sequential layers of different metals, for example, a base layer of silver combined with an upper layer of the gold for a total double layer thickness of between about 40 nm to about 70 nm. One of ordinary skill in the art can readily determine the appropriate thickness of the SPR supporting metal layer for a given SPR sensor application by varying the metal layer thickness to optimize the resonance curve.

Prior to adherence or deposition of the conducting layer, a base or adherence layer is optionally applied to the substrate surface. The adherence layer is typically a metal layer, such as chromium, nickel, platinum or titanium, less than about 50 Å thick, and more preferably about 20 Å thick.

The sensing area optionally contains one or more additional layers adhered to the SPR supporting conductive layer to yield a change in the effective refractive indices detectable by the sensor. Such additional layers can include a dynamic range-controlling layer, a reactive layer, a protective overlayer or any combination thereof. A variety of techniques are known and available to those in the art to provide dynamic range-controlling layers, reactive layers and protective layers in an SPR sensing area.

A "dynamic range-controlling layer" is a layer adhered to the SPR supporting conductive layer to alter the dynamic range of the SPR sensor. This layer has an index of refraction different (either higher or lower) than that of the SPR-supporting layer. For example, adherence of a layer of higher refractive index to the index of the substrate will extend the dynamic range of the sensor to include lower RI values. For example, U.S. Pat. No. 5,327,225, describes the use of an overlayer of relatively high refractive index material on a fiber SPR sensor with a silver SPR-supporting layer to shift the dynamic range of the sensor to a lower RI value.

A "reactive layer" is an optional layer in the SPR sensing area which interacts with a sample or an analyte species in the sample such that the effective refractive index detected by the sensor is altered. The addition of the reactive layer permits the manufacture of an SPR sensor which is more sensitive or selective for a sample (or analyte in a sample). Suitable reactive layers include those used in biological sensors, e.g., an antigen, antibody, nucleic acid or protein bound to the SPR supporting metal layer. This type of reactive layer will selectively bind a species in the sample, for example, a cognate antibody or antigen or complementary nucleic acid in the sample, increasing the thickness of the reactive layer and causing a shift in the effective refractive index measured by the sensor. Most generally, suitable reactive layers are altered in some way by contact with the sample so that the effective refractive index as measured by the sensor is changed. Reactive layers also include sol-gel films and polymer coatings.

Reactive layers can be adhered to the SPR-supporting conductive layer or to an overlayer on the conducting layer. The reactive layer should interface with the sample solution.

A number of methods have been described, are known and available to those of ordinary skill in the art, for the formation of reactive layers with sensitivity to a variety of biological or chemical species. Formation of the reactive layer on a metal layer may require an intermediate thin layer of material to passivate the metal or protect ligands in the reactive layer from reaction with the metal; For example, U.S. Pat. Nos. 4,844,613, 5,327,225, 5,485,277, and 5,492,840 disclose or summarize methods for preparation of such reactive layers in SPR sensors.

An SPR sensor of this invention can be configured with one or more sensing areas. One or more active sensing areas (those capable of detecting changes in RI of a sample) and one or more reference sensing areas can be provided in an SPR sensor. Active sensing areas in an SPR sensor can be provided with different reactive layers (e.g., can be functionalized for interaction with different biological or chemical species or functionalized differently for interaction with the same biological or chemical species), different over- or underlayers, different dynamic range-controlling layers and/or combinations thereof.

Multisensor Configurations

SPR sensing can be combined with other optical sensing technologies in the capillary geometry sensors of this invention. SPR sensing can be combined, for example, with critical angle refractometry, fluorescence and chemiluminescence techniques, absorption spectrometry and Raman scattering. The capillary simultaneously provides a geometry for multi-sensing and a configuration which has great potential for miniaturization, ruggedness, and ease of use. The capillary serves as a disposable, easily replaceable optical element and microvolume sample conduit/container, with an intrinsically protected sensor surface and an ideal flow geometry. A multisensor can be implemented using the capillary SPR geometry by providing for radial or axial and radial illumination of the capillary as illustrated in FIG. 6.

Figure 6:
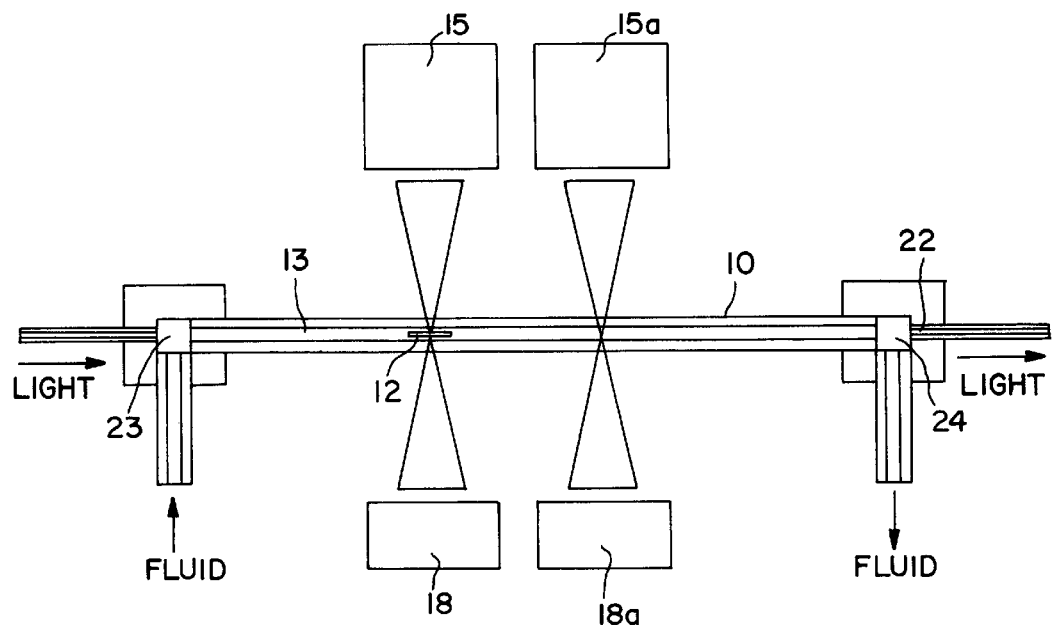
FIG. 6 is a schematic side-view illustration of a capillary SPR multisensor with axial and radial sensor illumination.

The multisensor of FIG. 6 has a capillary substrate (10) with at least one SPR-sensing area (12). At least one light source (15) is provided to provide for radial illumination of the capillary to obtain SPR data. The SPR-sensing area of the capillary is positioned to be illuminated by that radial light source (15). An optional second radial light source (15a) can be provided to obtain other optical data (which is discussed below). Additional radial light sources can be provided as desired. A detector (18) which detects light exiting radially from the capillary as a function of angle which may be a diode array is positioned to receive light reflected from the SPR sensing area at angles greater than the critical angle. Additional light detectors can be provided for detection of light radially exiting the capillary at a selected angle or range of angles (18a). In FIG. 6 radial illumination from both light sources is illustrated as focused at or near the capillary surface. As noted above focusing of the radial illuminating light is not required, but is preferred at least for SPR measurements. The relative position of the focus of the light source with respect to the capillary can be adjusted as discussed herein to provide illumination at a desired range of angles. A light source for axially illumination of the capillary (introduction of light into the capillary cavity) can also be provided. In the illustrated sensor configuration, optical fiber connections (21 and 22) to the capillary, one of which can be optically coupled to an appropriate light source and the other of which can be optically coupled to an appropriate detector, are provided. A separate light source for axial illumination and a separate detector for receiving light axially exiting the capillary can be provided. In alternative configurations, a single light source may be employed with appropriate optics for illuminating the capillary both radially and axially. Similarly, a single detector may be used again with appropriate optics for detecting light exiting the capillary both axially and radially. In a basic sensor configuration, each light source whether a radial or an axial light source is provided with an appropriately positioned detector. The capillary is also provided with fluid connections (23 and 24) for introducing samples into (and removing samples from) the capillary cavity. In a preferred embodiment, fluid flows through the capillary at a selected rate that allows desired optical measurements to be made. In the illustrated device, fluidic/optical connectors are employed to provide both optical and fluid coupling into and out of the capillary.

When radially illuminated, light strikes the internal wall of the capillary at angles ranging from 0° (normal incidence) to 90° (glancing incidence), corresponding to both transmission and evanescence in the lower-refractive index analyte inside the capillary. Thus, by changing the angles of illumination and modifying the internal surface of the capillary, several different sensing techniques can be implemented.

In a transparent capillary, low-angle transmission/emission measurements (e.g. for absorption or fluorescence measurement) and sub-critical angle reflection measurements (e.g. for bulk refractive index measurement) can be performed; in a capillary internally coated with an SPR-active metal, super-critical angle SPR reflection measurements can be performed. When axially illuminated, total internal reflection at the interface between the outer wall of the capillary and the air ambient turn the capillary and its contents into a light pipe; light cannot escape the capillary except through its ends, and is guided through the capillary, creating an ideal geometry for long-path length optical measurements such as fluorescence, chemiluminescence, absorption, and Raman scattering.

The capillary geometry has been applied in varying optical applications. The axial waveguiding properties of capillaries are well known (Wolfbeis, O. S., (1996), "Capillary waveguide sensors," Trends in *Analytical Chemistry* 15:225–232) and have been exploited for fluorescence (Kieslinger, D. et al. (1997), "Lifetime-based capillary waveguide sensor instrumentation, *Sensors and Actuators* B 38–39:300–304) and Raman scattering (Stellman, C. M. et al. (1998), "A fiber-optic pipette for rapid long-pathlength capillary spectroscopy," *Sensors and Actuators* B 46:56–60) measurements, among others. The radial optics of capillaries have been used in on-column detectors for capillary chromatography and electrophoresis, including an absorption detector (Boring. C. B. and Dasgupta, P. K. (1997), "An affordable high-performance optical absorbance detector for capillary systems, *Analytica Chimica Acta* 342:123–132) and two configurations of interferometric RI sensors (Krattiger, B. et al. (1993), "Laser-based refractive-index detection for capillary electrophoresis: ray-tracing interference theory," *Appl. Opt.* 32:956–965; Tarigan, H. J. et al. (1996), "Capillary-scale refractive index detection by interferometric backscatter," *Anal. Chem.* 68:1762–1770). The geometry of radial illumination of capillaries has been discussed above.

In a specific embodiment, the capillary SPR geometry sensor can be used to simultaneously measure SPR and bulk RI. To provide an improved SPR sensor with enhanced resolution that is particularly useful for measurement of biological molecules.

Light striking the interface between two media of differing RI will reflect from the interface, with reflectivity varying with incident angle. At high angles, reflectivity increases sharply, reaching 100% at the critical angle. The value of this angle varies with the RIs of the two media. If one medium has a fixed RI, measurement of the critical angle may be used to determine the RI of the other medium.

Critical angle refractometry may be used to overcome a major source of interference in SPR measurements: bulk RI effects. Because the sensitivity of SPR refractometry extends approximately one wavelength from the sensor surface—much thicker than many thin films of interest—the SPR sensor will also respond to changes in the RI of the bulk analyte adjacent to the thin film. This can create severe experimental difficulties. In biosensing, for instance, the bulk analyte will typically be a water-based buffer solution containing biologically active molecules. The RI of this solution will change with temperature and buffer concentration, and the sensor's response to these changes can easily exceed the thin-film response resulting from binding of biomolecules. The typical solution to this problem has been to control the temperature and concentration of the bulk analyte, to keep its refractive index as constant as possible.

A more versatile method of controlling interference from bulk effects combines the special features of SPR and critical angle refractometry. While both critical angle and SPR refractometry may be used to measure bulk refractive index, the response of the critical angle refractometer shows very little response to an adsorbed film. Because critical-angle refractometry is mostly insensitive to thin-film analytes, it may be used to measure the RI of the bulk analyte, independent of any thin film present.

SPR and critical angle refractometry (CAR) can be performed simultaneously, using a modification of the a known SPR sensor [See: U.S. Provisional Application, U.S. Ser. No. 60/132,894, filed May 6, 1999 which is incorporated by reference herein in its entirety to provide a description of a combined SPR/CAR sensor device and critical angle compensation methods]. In this method buffer concentration was intentionally changed during the experiment. Only the SPR measurement (surface RI) changes with antibody binding, while both the SPR measurement and critical angle measurement (bulk RI) respond to changes in buffer concentration. When compensated for bulk changes, the SPR response resolution improves. Critical angle compensation as described in U.S. Ser. No. 60/132,894 can be employed in the multisensors of this invention.

Figure 7:
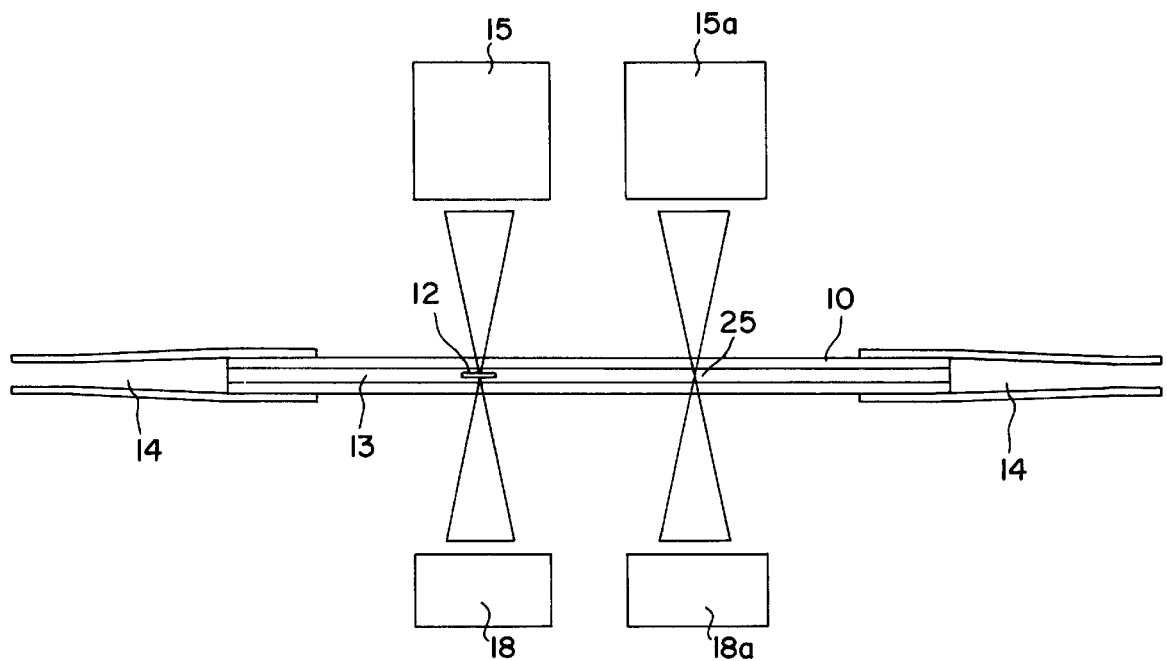
FIG. 7 is a schematic side-view illustration of a capillary SPR multisensor implementation of simultaneous SPR and critical angle sensing.

The combination of SPR measurements and critical-angle bulk refractive index measurements has great value, and is readily implemented in the capillary SPR geometry of this invention. An exemplary SPR/critical angle bulk refractive index capillary sensor is illustrated in FIG. 7. The illustrated sensor has a capillary substrate (10) which contains an SPR-sensing area (12) and bare regions (25) distributed axially. An alternative implementation of this combined sensor would have a capillary substrate with radial patterning of the SPR-conductive layer to provide inside surfaces of the capillary without a conductive layer (bare areas). The sensor is illustrated with two radial light sources (15 and 15a) and two detectors (18 and 18a). Light source 15 is positioned with respect to the capillary to illuminate the SPR-sensing areas and detector 18 is positioned with respect to the capillary to receive and detect light radially exiting the capillary that carries SPR data (light reflected at angles greater than the critical angle). The second light source 15a is positioned to illuminate a bare region of the capillary and the second detector is positioned to receive light radially exiting from the bare region. The second light source and detector provide allow measurement of critical angle bulk RI. In an alternate implementation, a single light source and a single detector with appropriate patterning of SPR-sensing areas on the inside surface of the capillary can be used to measure both SPR and critical angle bulk RI.

Label-free, multichannel SPR sensing is an extremely versatile technology which is the fundamental sensing principle implemented in the capillary multisensor. By combining the unique features of each technology, simultaneous implementation of multiple sensing technologies will enable immediate verification and cross-checking of SPR sensor data, provide the ability to compensate SPR sensor data against interference from nonspecific binding and bulk RI effects, and in general produce a sensor which provides more information about the analyte than any one technology alone. A description of sensor technologies (optical measurements), in addition to SPR and critical angle bulk RI measurements, that can be implemented in the capillary multisensor of this invention follows.

Interferometric refractometry. Both SPR and critical angle refractometry are reflectometric techniques-reflected light is measured. A transmission-based, interferometric method of bulk refractometry has been implemented in the capillary geometry by Tarigan et al. (Tarigan, H. J. et al. (1996), "Capillary-scale refractive index detection by interferometric backscatter," *Anal Chem.* 68:1762–1770). In this method, a capillary is illuminated with a collimated laser beam. The backscattered light has a complicated distribution resulting from the interference of multiple light paths reflecting inside the capillary. Some of the reflected rays pass through the analyte, and thus have optical paths which vary with the RI of the analyte, while other rays pass only through the walls of the capillary, and do not vary with the analyte. The interference of these rays creates a pattern of fringes which move with the RI of the analyte. Measurement of fringe position may be used as a sensitive measure of RI change in the analyte; a detection limit of $10^{-8}$ RI units has been reported. Prior to this work, a similar forward-scatter technique was developed by Krattiger et al. supra.

These interferometric techniques provide a measurement of bulk RI similar to that provided by the critical angle technique described above, and are useful for the same reasons. Furthermore, these techniques can be readily adapted in capillary SPR configuration to enable interferometric SPR measurements, which have been shown to have potential for increased sensitivity (Nikitin, P. I. et al. (1999), "Surface plasmon resonance interferometry for biological and chemical sensing," *Sensors and Actuators* B 54:43–50).

Fluorescence and Chemiluminescence. These well-established label-based sensing techniques can provide verification and augmentation of SPR measurements. For instance, after an SPR measurement indicates that a certain antigen has bound to the sensor surface, fluorescent-labeled antibody can be passed through the sensor. Observation of fluorescence from bound labeled antibody then confirms the presence of the antigen on the sensor surface.

Figure 8A:
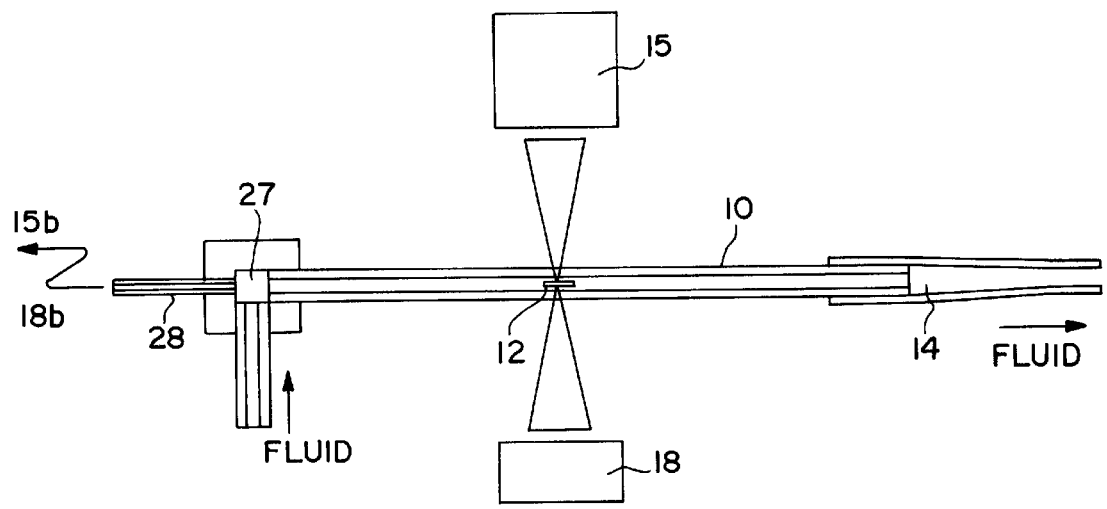
FIGS. 8a and 8b are schematic side-view illustrations of capillary SPR multisensor implementations for simultaneous SPR and fluorescence sensing. In the multisensor of FIG. 8a, fluorescence is axially excited and axially detected. In the multisensor of FIG. 8b, fluorescence is radially excited and axially detected.

Two exemplary multi-sensor configurations are shown in FIGS. 8*a* and *b*. In FIG. 8*a*, SPR is measured radially, while fluorescence is excited and collected axially. The sensor has a capillary substrate (10) with an SPR-sensing area (12). A radial light source 15 and a detector 18 for detection of radially exiting light to measure SPR are provided. Light is axially coupled into and exiting light coupled out of the capillary cavity via an optical fiber (28) through a fluid/optical coupler (27). Fluid/optical coupler (27) and tubing connection (14) provide for sample introduction and removal from or sample flow through the capillary cavity. The fluorescence excitation light source (15*b*) and axial fluorescence detector (18*b*) are optically coupled to the optical fiber (28).

Figure 8B:
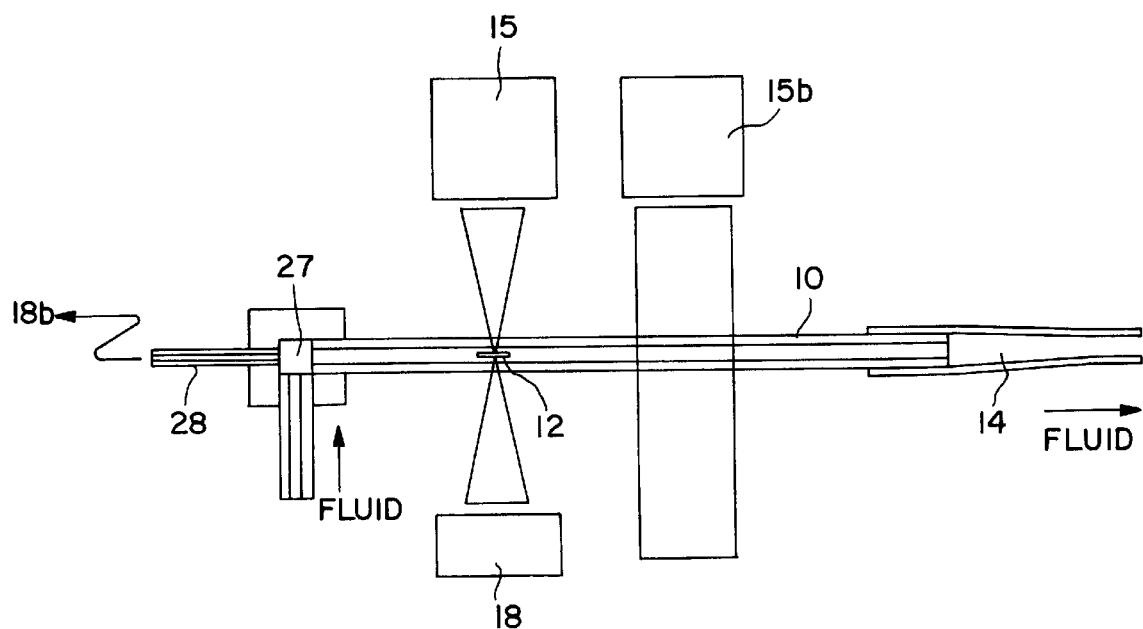

In the multisensor of FIG. 8*b*, SPR is measured radially and fluorescence is excited radially and measured axially. Radial light source 15 and detector 18 are provided for measuring SPR. A fluorescence excitation source (15*b*) is radially coupled into the capillary cavity. Fluorescence is collected axially via a fluid/optical connector (27) coupled to a detector (18*b*) via an optical fiber (28). This configuration has the advantage that the excitation light is perpendicular to the capillary, and so will tend not to be collected. Other configurations can also be implemented; for instance, fluorescence may be collected radially with the aid of an elliptical mirror (Kao, H. P. and Schoeniger, J. S. (1998), "Elliptical trough reflector for the collection of light from linear sources," *Appl. Opt.* 37:4194–4199).

Raman spectroscopy and absorption. These optical measurement techniques are generally used for very different applications than SPR and fluorescence, but are readily implemented in the capillary geometry.

Selective patterning of SPR-sensing area on the inside surface of the capillary can be accomplished using various methods. For example, the region or regions coated with metal on the inside surface of the capillary can be controlled in the wire deposition method by selective coating of the tungsten wire. This method can be used, for example, to fabricate a capillary which is axially patterned, e.g., metal-coated for a portion of its length and uncoated for another portion.

Uniform wet-chemical functionalization of the interior capillary surface is achieved by flowing the appropriate series of reagents through the capillary. One simple approach for creating multiple areas of different functionalization is to insert reagents at different locations in the capillary using a needle (Evensen, H. T. et al. (1998), "Automated fluid mixing in glass capillaries," *Rev. Sci. Instrum.* 69:519–526). However, long or very narrow capillaries cannot be easily treated by this technique. If only two differing regions of functionalization are needed, a two-sided injection technique may be used, in which reagents are drawn partway into the capillary, allowed to rest there for the required time, and then ejected. By repeating this procedure for both sides of the capillary, two separately functionalized regions can be created. Sophisticated automatic control of fluid volumes in capillaries such as that demonstrated by Evenson et al. (Misiakos, K. and Kakabakos, S. E., (1998), "A multi-band capillary immunosensor," *Biosensors & Bioelectronics* 13:825–830) can be used to automate this task.

Infrared waveguides have been implemented by using chemical vapor deposition (CVD) to deposit multiple dielectric layers inside of silica capillaries (Matsuura, Y. and Harrington, J. (1997), "Hollow glass waveguides with three-layer dielectric coating fabricated by chemical vapor deposition," *J Opt. Soc. Am. A* 14:1255–1259). This versatile deposition technique can be used to fabricate capillary sensors.

Removal and resist techniques can also be used for patterning inside glass capillaries. Removal techniques may be used when, in addition to reagents for depositing layers inside the capillary, there are reagents to remove such layers (e.g. aqua regia for gold layers, NaOH for proteins). Controlled injection of these reagents provides a simple method for axial patterning inside capillaries by which any number of distinct regions may be created (Weigl, B. H. and Wolfbeis, O. S. (1994), "Capillary optical sensors," *Anal Cliem.* 66:3323–3327).

Resist techniques provide another strategy for axial and radial patterning inside capillaries. The wall of the capillary is coated with photoresist polymer, partially exposed to UV light, and developed, leaving a photoresist pattern on the interior surface of the capillary. After the desired layers are deposited, the photoresist is removed, leaving a patterned layer on the capillary surface. This technique may be applied to radial patterning of gold layers.

In one exemplary implementation, a capillary is filled with a UV-opaque fluid prior to exposure. Thus, only one side of the capillary wall is exposed, leaving a hemicylindrical resist pattern inside of the capillary after development. If gold is then deposited and the photoresist removed, a hemicylindrical gold layer remains. This technique requires that the photoresist chemistry and the layer deposition chemistry be compatible, which is likely to limit its application in the deposition of biologically active layers. For these layers, photoactivatable silanes (Conrad, D. W. et al. (1997), "Photoactivatable silanes for the site-specific immobilization of antibodies," *Proc. SPIE* 2978:12–21) are likely a more useful method of patterning.

A field-based capillary sensing instrument should be capable of robust, real-time data analysis. Chemometric techniques (Johnston, K. S. et al. (1997), supra), combined with estimation theory (Chinowsky, T. M. et al. (1999), "Optimal linear data analysis for surface plasmon resonance biosensors, *Sensors and Actuators* B 54:89–97; Chinowsky, T. M. and Yee, S. S. (1998), "Quantifying the information content of surface plasmon resonance reflection spectra," *Sensors and Actuators* B 51:321–330) can be applied to design optimal data analysis techniques for the capillary sensor. The instrument should require little user intervention: It should be self-calibrating, and any required optical alignment must be automatic. The sensing element must be easily replaceable; in the envisioned instrument, replacement of the capillary would be as simple as attaching connectors to either side of the capillary and clipping it into place. No index matching liquid or flow-cell assembly would be required.

The capillary SPR sensor and multisensors can be employed in a variety of sensing applications for the detection and quantitation of various chemical and biological species. The sensors of this invention can in general be used for any sensing application for which currently known SPR devices are employed. The SPR sensors and multisensors of this invention are particularly useful for applications as detectors in instrumental effluent streams, and more particularly as detectors in instruments that employ capillary separation techniques, including HPLC instruments.

The invention also relates to analytical kits which contain one or more capillary sensor substrates each having one or more SPR-sensing areas on the inside surface of the capillary. Capillaries in such kits can be made of soft glass or other inexpensive materials so that they are disposable. Kits also optionally include control samples of analytes of interest, e.g., for a selected sensing application, for sensor calibration. Kits may also be provided with fluid or optical connectors for introduction of a capillary sensor into an SPR sensor or multisensor. Kits can be provided with instructions for conducting SPR analysis or multisensing analysis using the capillaries in the kit. In a specific embodiment, a kit can contain a set of SPR capillary substrates each having one or more SPR-sensing areas which in turn carry one or more reactive layers for selective detection of one or more analytes. For example, a kit can be provided for selective detection of certain biological molecules, e.g., certain nucleic acids, certain proteins, certain antigens, etc. In an alternative embodiment, a kit can be provided with one or more capillaries each carrying one or more SPR-sensing areas and reagents for selectively depositing reactive layers on the SPR-sensing areas.

The following examples are intended to further illustrate the invention and are not intended to limit the invention.

THE EXAMPLES

Example 1: Preparation of SPR Sensing Areas

A. Electron Beam Evaporation

Glass tubing (3 mm OD/1.8 mm ID) was placed in an electron-beam evaporator and oriented at an angle 5° from vertical with respect to the evaporator. Following deposition of a chromium adhesion layer, sufficient silver was evaporated to produce a ~50 nm layer on the internal surface of the capillary. Angles from 1 to 10° from the vertical can be used to deposit the desired metal layer.

B. Wire Evaporation

Glass capillaries (Friedrick & Dimmock, 1 mm OD; 0.4 mm ID, about 2 cm long) were treated on their interior surface with 3-mercaptopropyltrimethyl silane to promote gold adhesion. See: Lyon L A et al. (1999) Sensors Actuators B 54:118–124. Gold was then deposited on the inside surface of the capillary using 2 mil Au-coated tungsten wire (Alfa Aesar). The wire was positioned in the center of the capillary cavity and held taut with micropositioners. A current pulse from a capacitance discharge was sent through the wire, heating the wire and evaporating gold onto the interior surface of the capillary. The wire contained 3–5% by weight of gold. Deposition was not uniform on the interior surface, but since only a small spot of gold is needed for SPR measurements, an area of suitable thickness (preferably about 50 nm) was readily found. Considering the amount of gold in the wire, it is estimated that a uniform layer of about 64 nm of gold would have been deposited by the method used.

C. Wet Chemical Deposition

The method of Lyon L A et al. (1999) supra was adapted for use with the internal surfaces of capillaries by pumping the necessary reagents through the capillary cavity using air pressure.

Metal layers (e.g., gold and/or silver) that support SPR can be made inside of capillaries of dimensions useful in the sensors of this invention by each of the methods of Example 1A–C.

A variety of methods known in the art can be employed to provide optional reactive layers in the capillaries of this invention at SPR-active conducting layers.

The SPR-conducting layers and any reactive layers can be selectively patterned on the interior surfaces of the capillary using a variety of methods that are known in the art. For example, removal and resist techniques may be employed.

Example 2: Demonstration of SPR Sensing in the Capillary Geometry

A capillary sensor substrate prepared as in Example 1A was placed in an optical apparatus similar to that shown in FIG. 2b and attached to a peristaltic pump so that fluids could be introduced into the capillary cavity. Air (n=1.00), water (n=1.33), and ethylene glycol (n=1.42) were then flowed through the tube while spectra from a diode array detector were recorded. The results of this SPR assay are shown in FIG. 7. The figure illustrates reflectivity (light intensity) accumulated as a function of increasing pixel number (of the diode array) which correlate with higher angles of incident light. An attenuation feature is observed which shifts to higher angles as the RI of the sample increases.

Those of ordinary skill in the art will appreciate that methods, materials and techniques other than those specifically discussed herein can be readily employed or adapted to implement the sensor configurations and practice the methods of this invention. For example, a variety of means for measuring reflection coefficients and/or light intensity are well-known and available to those in the art. In addition, there are a variety of techniques and devices known for collimating, collecting, expanding, magnifying, focusing and conducting light that can be applied or readily adapted to light input to or light output from the sensors of this invention. Those of ordinary skill in the art can readily select from among such alternatives, variants and functional equivalents those that are appropriate for use in the SPR configuration of this invention.

All of the references cited in this specification are incorporated by reference in their entireties herein.

We claim:

1. An SPR sensor comprising a capillary tube for receiving an analyte wherein a portion of the inside surface of the capillary tube has an SPR-supporting conductive layer.

2. The SPR sensor of claim 1 wherein SPR-supporting conductive layer is a metal layer.

3. The SPR sensor of claim 1 further comprising an adherence layer between said SPR-conductive layer and said inside surface of said capillary tube.

4. The SPR sensor of claim 1 further comprising a reactive layer covering at least a portion of the SPR-supporting conductive layer.

5. The SPR sensor of claim 4 wherein the reactive layer comprises biologically reactive species.

6. The sensor of claim 1 further comprising a light source that provides a TM-polarized component for radially illuminating the capillary tube.

7. The sensor of claim 6 wherein the light source is a laser diode.

8. The sensor of claim 1 further comprising a detector for detecting light radially exiting the capillary tube.

9. The sensor of claim 8 wherein the detector measures the intensity of reflected light at a range of angles.

10. The sensor of claim 8 wherein the detector is a diode array.

11. The sensor of claim 1 further comprising a lens for focusing incident light at or near the inner surface of the capillary.

12. A method for measuring SPR resonances of an analyte which comprises the steps of introducing the analyte into the capillary of the sensor of claim 1, radially illuminating the capillary and detecting light radially exiting the capillary tube.

13. A method for measurement of SPR of an analyte in a sample which comprises the steps of introducing a sample containing an analyte into the capillary cavity of the capillary tube of an SPR sensor of claim 1, illuminating the sample radially with light comprising a TM component and detecting light radially exiting from the capillary to detect SPR of the analyte.

14. A multisensor which comprises:
(a) a capillary tube for receiving an analyte wherein a portion of the inside surface of the capillary has an SPR-supporting conductive layer and a portion of the inside surface of the capillary is bare;
(b) a light source for radially illuminating the capillary;
(c) a detector for detecting light radially exiting the capillary.

15. The multisensor of claim 14 which measures SPR-and critical angle bulk RI.

16. The multisensor of claim 15 further comprising a light source axially coupled into the capillary.

17. The multisensor of claim 16 further comprising a detector axially coupled into the capillary.

18. The multisensor of claim 14 comprising more than one light source for radially illuminating the capillary.

19. The multisensor of claim 14 comprising more than one detector.

20. The multisensor of claim 14 which measures SPR and fluorescence and which further comprises a fluorescence excitation light source coupled radially into the capillary.

21. The multisensor of claim 20 which further comprises a fluorescence detector axially coupled into the capillary.

22. The multisensor of claim 14 which measures SPR and fluorescence and which further comprises a fluorescence exitation light source and a fluorescence detector coupled into the capillary.

23. The multisensor of claim 14 which measures SPR and absorption and which further comprises a light source and detector axially coupled into the capillary.

24. A method for measurement of SPR of an analyte in a sample which comprises the steps of introducing a sample containing an analyte into the capillary cavity of the multisensor capillary sensor of claim 14, illuminating the sample radially with light comprising a TM component and detecting light radially exiting from the capillary to detect SPR of the analyte.

25. The method of claim 24 wherein the bulk RI of the sample is measured and employed for critical angle compensation to enhance resolution of the SPR measurement.

* * * * *

UNITED STATES PATENT AND TRADEMARK OFFICE
CERTIFICATE OF CORRECTION

PATENT NO.     : 6,480,282 B1
DATED          : November 12, 2002
INVENTOR(S)    : Chinowsky et al.

It is certified that error appears in the above-identified patent and that said Letters Patent is hereby corrected as shown below:

Column 1,
Line 11, please insert -- STATEMENT REGARDING FEDERALLY SPONSORED RESEARCH This invention was made with United States government funding through the National Oceanic and Atmospheric Administration of the Department of Commerce under Grant No. NA76RG0119. The United States government has certain rights in this invention. --
Line 33, please delete "(3)".

Column 5,
Line 42, please delete "Lo".

Column 14,
Line 14, please delete "the".
Line 49, please delete "provide".

Column 16,
Line 48, please replace "Cliem." with -- Chem. --.

Column 18,
Line 41, please replace "FIG. 7." with -- FIG. 5. --.

Signed and Sealed this

Twenty-seventh Day of January, 2004

JON W. DUDAS
*Acting Director of the United States Patent and Trademark Office*